United States Patent [19]
Lerch et al.

[11] Patent Number: 5,895,704
[45] Date of Patent: Apr. 20, 1999

[54] ARTICLE FOR COLLECTING AND TRANSPORTING A SAMPLE TO BE ANALYZED

[75] Inventors: Rolf Lerch, Ilvesheim; Gregor Bainczyk, Mannheim; Hans Wielinger, Weinheim, all of Germany; Jack Bush, Fishers, Ind.

[73] Assignee: Boeringer Mannheim GmbH, Germany

[21] Appl. No.: 08/757,374

[22] Filed: Nov. 27, 1996

Related U.S. Application Data

[60] Provisional application No. 60/007,549, Nov. 27, 1995.
[51] Int. Cl.⁶ ..................................................... G01N 21/00
[52] U.S. Cl. .................. 428/195; 428/411.1; 428/488.1; 428/204; 428/192; 422/56; 422/57; 422/58; 435/4
[58] Field of Search ........................ 428/195, 411.1, 428/488.1, 204, 192; 422/56, 57, 58; 435/4

[56] References Cited

U.S. PATENT DOCUMENTS

| | | |
|---|---|---|
| 4,273,741 | 6/1981 | Levine . |
| 4,789,629 | 12/1988 | Baker et al. ........................ 435/7 |
| 5,118,609 | 6/1992 | Baier et al. . |

FOREIGN PATENT DOCUMENTS

| | | |
|---|---|---|
| 583078 | 7/1993 | European Pat. Off. . |
| 9209639 | 4/1992 | Germany . |
| 2031583 | 8/1978 | United Kingdom . |
| 9003927 | 4/1990 | WIPO . |

*Primary Examiner*—Richard Weisberger
*Attorney, Agent, or Firm*—Fulbright & Jaworski, LLP

[57] ABSTRACT

The subject of the invention is an article for collecting and transporting a sample to be analyzed; containing an absorbent matrix to absorb a liquid sample, characterized in that the absorbent matrix represents the sample collecting area of a sample collecting element, which is an integral part of an envelope. In addition, the subject of the invention is a process for determining an analyte, in which liquid sample material is placed on an absorbent matrix, dried, sent to a laboratory and tested there, characterized in that the liquid sample material is placed on an absorbent matrix that represents the sample collecting area of a sample collecting element, which is an integral part of an envelope.

18 Claims, 3 Drawing Sheets

5,895,704

ARTICLE FOR COLLECTING AND TRANSPORTING A SAMPLE TO BE ANALYZED

This application claims benefits of Provisional Application 60/007,549 filed Nov. 27, 1995.

The invention relates to an article for collecting and transporting a sample to be analyzed, containing an absorbent matrix for soaking up a liquid sample, as well as a process for determining an analyte in which the liquid sample material that is suspected of containing an analyte to be determined is placed on an absorbent matrix, dried, then sent to a laboratory and tested there.

From the state of the art, square cards of filter paper are known as sample collecting elements, onto which the whole blood to be tested is dropped and dried. Then these cards are placed in an envelope and sent to a laboratory where the dried blood samples are tested. To do this, a round part of the filter paper containing the blood is punched out and the analyte to be determined is eluted from it and then detected and measured according to known methods. Sample collecting elements of this type are known, for example as "Guthrie test cards," which are used to collect, transport and analyze the blood of newborns. Corresponding cards are produced and marketed, for example by the companies Schleicher & Schüll, Dassel, Germany or Whatmann, Maidstone, England. One example of such a card is shown as an example in FIG. 1A. The previously known sample collecting elements consist of filter paper of cellulose. The disadvantage of this material is that the test substance is not uniformly distributed in the blood drop on the paper. The so-called chromatography effect causes the test substance to migrate more heavily to the edge of the drop and therefore not be distributed uniformly in the area of the dried drop. In the laboratory, as already described, a part of the sample collecting area on which the blood is placed, is stamped out and eluted. Because of the chromatography effect, the result that is obtained often depends on what part of the dried blood drop is stamped out and eluted.

With the filter paper materials that are currently used, the absorption times are also very lot-dependent, i.e. sometimes a drop of blood is quickly absorbed, sometimes a blood drop of the same size is absorbed significantly more slowly. During slow absorption of the blood drop, it is possible that the blood drop can get smeared if the sample collecting element is not handled carefully.

Another disadvantage of the previously known blood collecting cards of filter paper is that elution of the sample material takes a long time, 40 minutes to 1 hour, as a rule.

The filter papers of cellulose fibers used for the Guthrie test cards also absorb a relatively large quantity of humidity from the air. This can lead to significantly false positive values with certain analytes. For example, in the determination of $HbA_{1c}$, values can be found that are excessive by 100 to 200%.

An $HbA_{1c}$ sample collecting element is known from Klin. Lab. 1993/39, Pages 1080 to 1082, in which a cellulose base filter paper lies below the cut-out of a hydrophobic paper. A drop of blood is placed in the cut-out and dried. The test card is placed first in a plastic bag and the plastic bag with the sample collecting element is then placed in an envelope for sending to the laboratory. With the use of this and the sample collecting elements described above, there is always a danger of contamination because of the handling steps required of the patient and in the laboratory. Contamination is particularly problematic when the test card is slid into the plastic bag or the envelope and when the test card is taken out of the bag or envelope. In addition, storage of several components causes higher costs and more work than storing fewer components. This can lead to individual parts getting lost which may then be replaced by other parts that are available, but not optimally adapted to the task.

The object of the invention was to prevent these disadvantages. This was done by the object of the invention, as it is designated in the patent claims. The object of the invention is an article for collecting and transporting a sample to be analyzed that includes an absorbent matrix for soaking up a liquid sample, wherein the absorbent matrix contains the sample collecting area of a sample collecting element, which is an integral component of an envelope. The sample collecting element and the material that is used to package the sample collecting element consequently form a unit according to the invention. In the scope of the present invention, any material can be designated as an envelope, which is suitable for surrounding and covering the sample collecting element so that it is no longer possible to come in contact with the sample collecting area during handling when the envelope is closed. However, an envelope that is made like an envelope for a letter is particularly preferred, in which the sample collecting element is integrated in the back side of the envelope. For better handling in the laboratory, the limits of the sample collecting element can be prepared in such a way that the sample collecting element can be separated from the envelope in a pre-determined manner. This can be effected by adding target breaking or tearing lines, along which the sample collecting element can be separated from the envelope. Such target breaking and/or tearing lines can be formed by appropriate perforations or by the fact that the envelope material has a thinner material cross section than the surrounding material. Perforations are especially preferred.

The sample collecting element is that part of the article according to the invention that carries the sample collecting area with the absorbent matrix. The sample collecting area is that part of the absorbent matrix on which the liquid sample can be placed. It is advantageous if the absorbent matrix is below a cut-out on the sample collecting element so that the sample can only get onto the absorbent matrix through this cut-out. It is advantageous if the absorbent matrix is fastened to the back of the sample collecting element, most especially glued on, so that the base extends completely under the cut-out. The cut-out can have any conceivable shape. A round hole has proven to be especially preferred.

In a particularly preferred embodiment of the article according to the invention, the sample collecting area and thus the absorbent matrix consists of a material other than that of the sample collecting element. In this way, at least the part of the sample collecting element that surrounds the sample collecting area absorbs liquid less well than the matrix of the sample collecting area. In an especially preferred embodiment, the absorbent matrix consists of absorbent fleece and the remaining part of the article according to the invention of paper or cardboard, which are preferably treated so that the liquid is not absorbed or absorbed only poorly. However, also plastic can be considered for the envelope, or in general any material that fulfills the requirements of the invention. Basically, any envelope materials can be considered that correspond to the "Guidelines for the Shipment of Dried Blood Spot Specimens" of the U.S. Department of Health & Human Services dated May 1993.

A fleece containing synthetic fibers has proven to be especially useful as an absorbent matrix. Fleeces, such as described in U.S. Pat. No. 5,118,609 as a carrier fleece for removably impregnated reagents have proven to be particularly suitable. Accordingly, a fleece is particularly preferred that has a) cellulose base fibers, b) polymer fibers of polyester and/or polyamide base and c) an organic binder containing OH and/or ester groups. With a fleece like this, the chromatography effect is largely suppressed so that upon application of blood in the dried blood drop, the blood contents are uniformly distributed in the sample collecting area. The sample collecting area can be eluted very quickly with an absorbent matrix of this type. 10 to 20 minutes elution time is enough for complete elution of hemoglobin, including $HbA_{1c}$. In addition, fleece as described above have only very little hemolyzing effect, which prevents falsification of the measurements due to blood cell contents. Another advantage consists of the fact that a fleece according to the invention with synthetic fibers absorbs only relatively little humidity. This is also advantageous in determining correct quantitative analyte values. In addition the properties, in particular absorption properties, are hardly lot dependent, so better reproducible results can be achieved as was possible with the state of the art.

If necessary, the absorbent matrix of the article according to the invention can carry substances i.e. to increase wetting capability or for stabilizing the analyte to be determined. In particular, substances for stabilizing the analytes to be determined can be contained in or on the matrix. In a simple case, the matrix can be impregnated with the buffer of a specific pH value.

In a preferred embodiment of the article according to the invention, it is planned that certain data can be entered on the sample collecting element, e.g. patient data and data on the treating physician. Room for entering sample data can also be provided. In an especially preferred embodiment, the sample collecting element can have at least 1 label that can be used for sample identification. For example, this label can have a bar code in which data, e.g. name of the patient, sex, analyte to be determined are keyed, or other characteristics that can be used to identify the sample. In an extremely suitable embodiment of the article according to the invention, the sample collecting element has 2 labels with identical data. At least 1 label can be removed from the sample collecting element.

In addition, the sample collecting element can also have a temperature and/or humidity sensor in order to recognize whether the sample was exposed to a damaging temperature and/or humidity influence before the analysis. Appropriate sensors can be found, for example, in the form of stick-on labels that use color changes to show what temperature and/or humidity the sample element was exposed.

In order to mark the sample collecting area, it has proven to be especially user friendly if the area around the sample collecting area is designed so that it is visually striking. This can be done, for example, by using a noticeable color. In an especially preferred embodiment, at the location of the sample collecting element where the sample collecting area is located, a red mark in the form of a blood drop is applied. The cut-out in the sample collecting element is located at the thickest point of this spot, which is made visible by the white sample collecting area of the matrix. If another liquid is to be applied to the sample collecting element, the sample collecting area can be marked by a pictogram of this other sample material.

It is also possible to slightly raise the area surrounding the sample collecting are using an inert material, so that the probability of contact of the inside of the closed side of the envelope with the absorbent matrix of the sample collecting element and contamination of the closing flap is prevented still more. For example, a plastic ring or cardboard that surrounds the sample collecting area can be used as inert material.

As is known from standard commercial envelopes for letters, the article according to the invention can be provided with adhesive to close the envelope. Adhesive can be present such a way that it is dry and becomes sticky by being moistened. The adhesive can also be covered with a strip that is easy to pull off and reveals the sticky adhesive after it is pulled off. Preferably, the adhesive is applied to the back side of the closing flap of the envelope in such a way that when the envelope is closed, it comes in contact with the back side of the envelope outside the sample collecting element. Basically it is also possible to provide the closing flap with a quasi-3-sided adhesive around the circumference so that the envelope can be closed on all sides.

In the preferred embodiment of the article according to the invention, the envelope has perforations arranged parallel to and below the adhesive, most particularly preferred are two lines of perforations arranged in parallel which make it possible to separate the envelope at this point.

Instead of perforations, one or two parallel lines with thinner material cross section can be used as target breaking and/or target tearing points. The target breaking and/or target tearing points offer the advantage that the closed envelope can be opened easily and without danger of contamination so that the sample collecting element is easily accessible and can be taken out.

FIG. 1A shows a view of a Guthrie test card as state of the art sample collecting element.

FIG. 1B shows a view of the back side of a standard commercial envelope for a letter, in which the Guthrie test card can be placed and sent.

FIG. 2A shows a view of an article according to the invention that is open and ready to hold the sample.

FIG. 2B shows a view of an article according to the invention, closed and ready for transport after the sample has been applied.

Figure 1A:
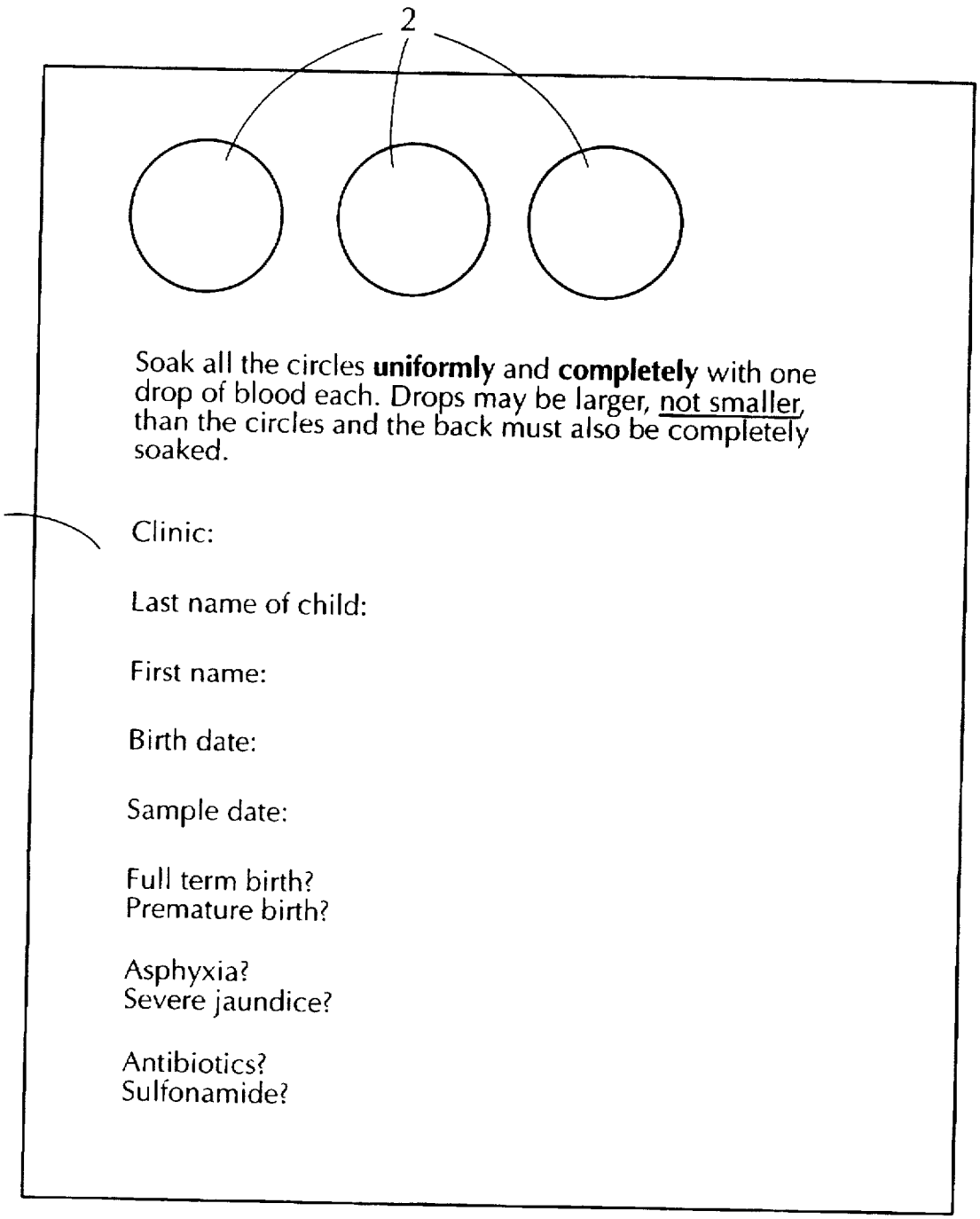
FIGS. 1A and 1B show a sample collecting element and envelope according to the state of the art.

FIG. 1A shows a Guthrie test card (1) that is used as a sample collecting element for the blood of newborns. The entire sample collecting element consists of the same filter paper material. The sample collecting areas (2) are marked by black circles on the white filter paper. Below the sample collecting areas (2) there are recommendations addressed to the person applying the sample. The remaining area on the test card (1) is for data to identify the clinic, the person giving the sample, the sample and possibly diseases and/or treatments of the person giving the sample.

Figure 1B:
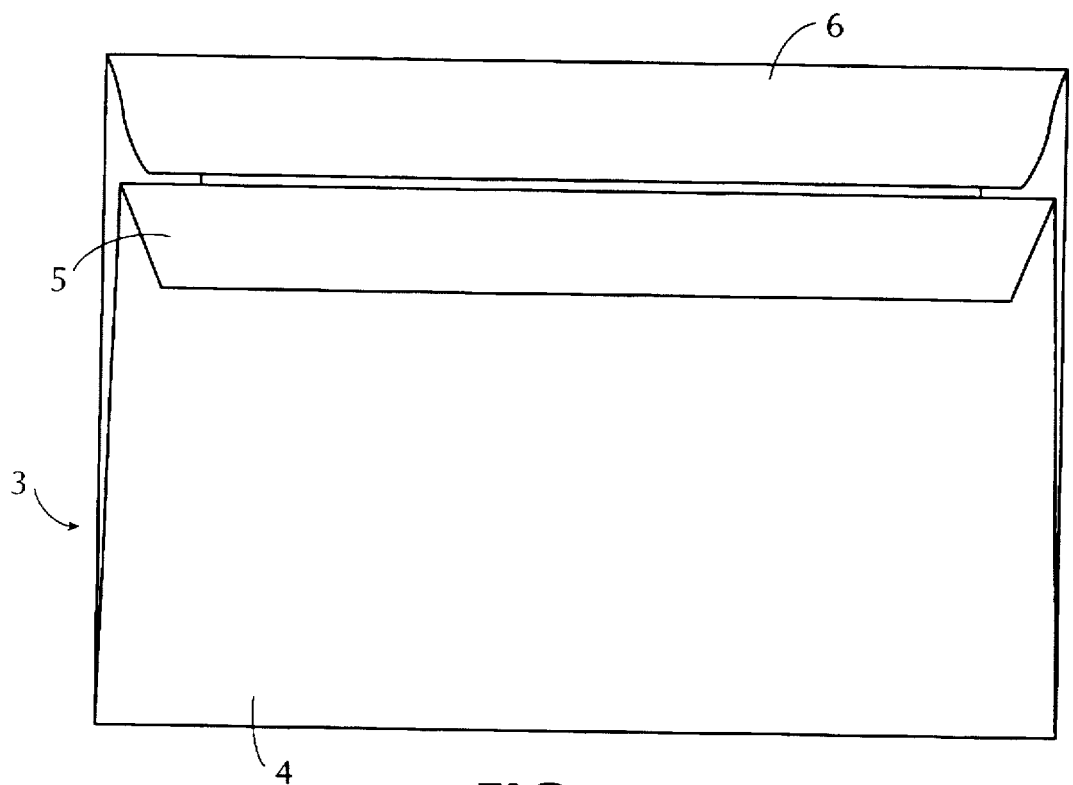

After sampling, application of the liquid sample and drying of the sample, the Guthrie test card (1) is first packed in a plastic bag and then placed in a standard envelope for a letter (3), the back (4) of which is shown in FIG. 1B. To close the envelope (3), the flap (5) of the back (4) is folded up and placed under the closing flap (6). Both flaps (5,6) are coated on the bottom with material that has an adhesive effect when brought into contact with the other. Therefore, the envelope (3) is closed with adhesive when the flap that is folded up (5) and the flap that is folded down (6) are pressed together. The envelope closed in this way is then sent to the testing laboratory.

Figure 2B:
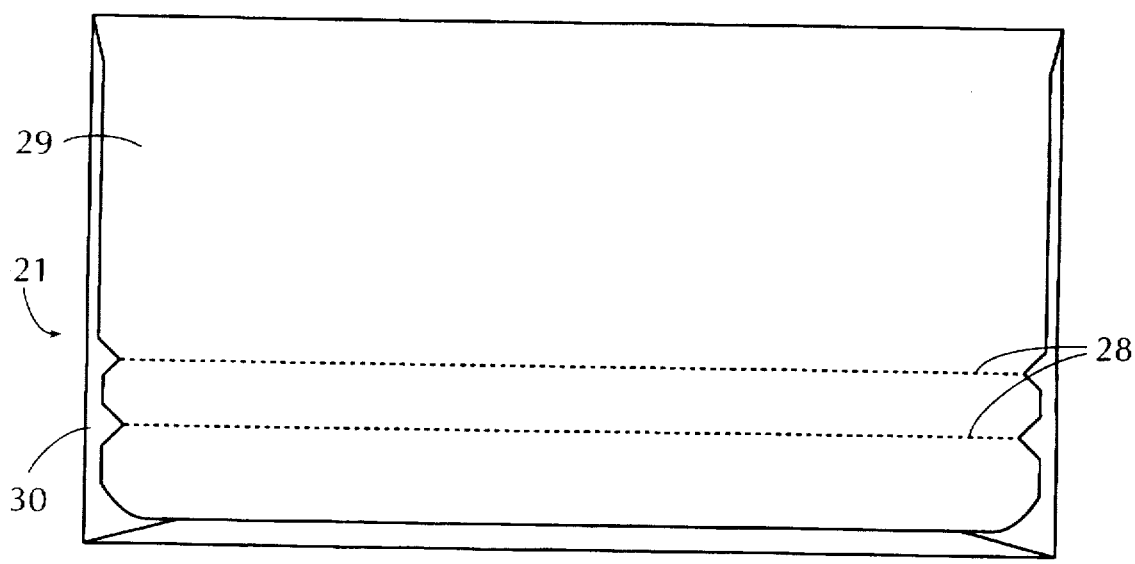
FIGS. 2A and 2B show a particularly preferred article according to the invention.
Figure 2A:
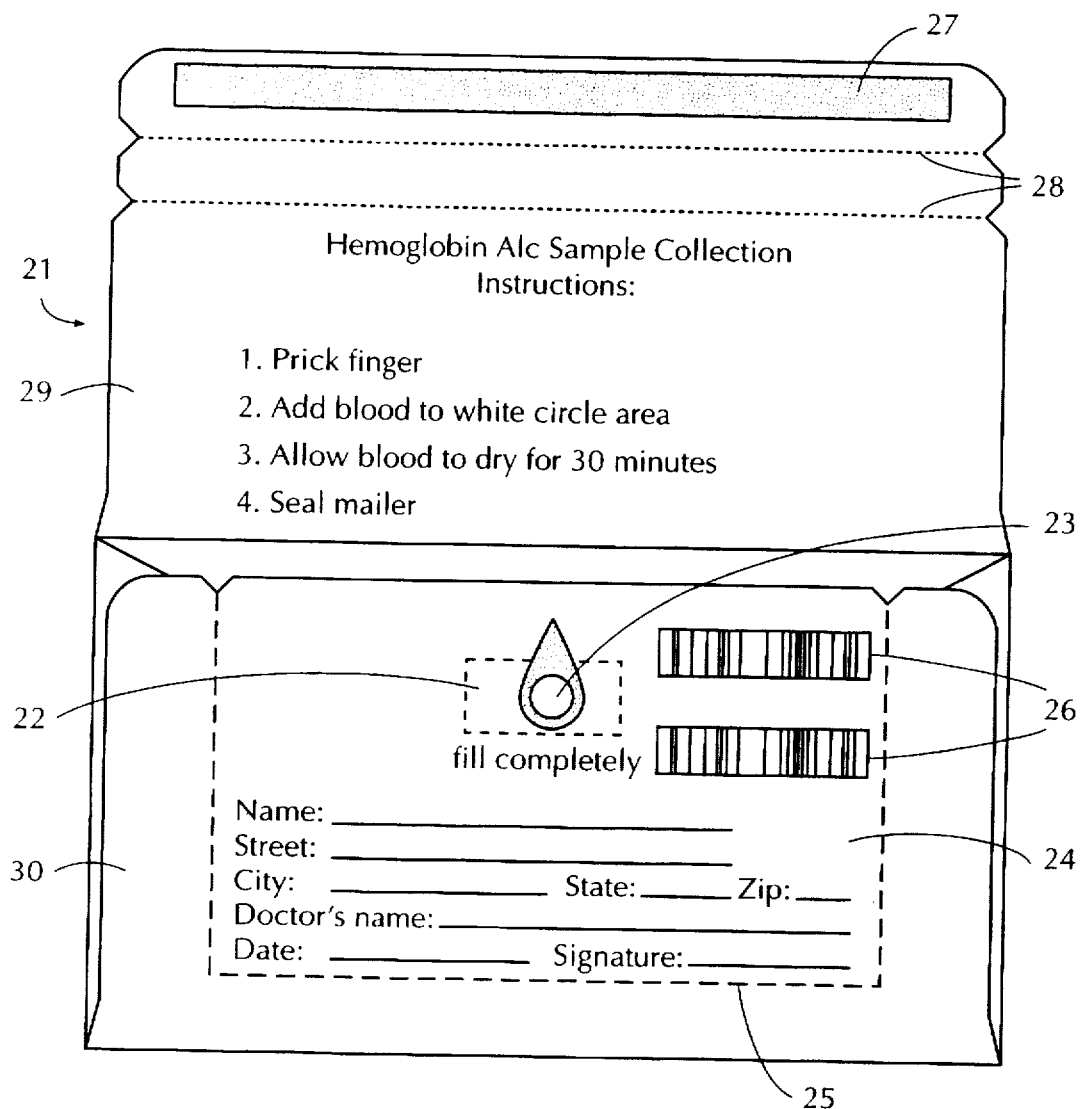

FIG. 2A shows an article according to the invention for collecting and transporting an $HbA_{1c}$ sample. This analyte represents only a preferred example. Samples for determining other analytes can also be collected and transported with the article according to the invention. Basically this applies to all analytes that are brought into solution by corresponding elution agents and can then be measured in this solution. Basically these are all analytes that can also be determined using immunological test procedures. Without wanting to restrict the circle of possible analytes, those analytes should also be mentioned at this point that are used for detecting infectious diseases, e.g. virus antibodies or virus components for determination of hepatitis and HIV.

The article according to the invention shown in FIG. 2A has the shape of an envelope (21) suitable for postal use. On the front side of the envelope, an address is preprinted or there is room to enter an address. The back (30) of the envelope (21) has the sample collecting element (24), on which there is space to enter the patient address and the treating physician or clinic. The sample collecting element (24) is marked with a perforated line (25) and limited from the rest of the article according to the invention surrounding it by this perforated line (25). The perforation (5) |sic| makes it easier later to take the sample collecting element (24) out in the laboratory.

At a central point on the sample collecting element (24), there is the sample collecting area (23). It is designated with a round hole in the sample collecting element (24) and emphasized visually by a surrounding drop-shaped mark. Under the sample collecting area (23), there is an absorbent matrix (22), the contours of which are shown in dotted lines on FIG. 2A. The size of the sample collecting area (23) depends on the sample quantity needed for the analysis, which is applied to the absorbent matrix (22) and has to be collected there. As a rule, the sample collecting area (23) has a diameter from 5 to 20 mm. The matrix (22) placed below the sample collecting area accordingly has a rectangular or square shape, in which the edge lengths are about 5 to 20 mm larger than the greatest extension of the sample collecting area (23). A fleece with weight per surface area of about 60 g/m$^2$ is especially suitable as the absorbent matrix (22), which is produced in the following way. The process uses a oblique wire cloth machine (Voith, Heidenheim, Germany) as is used for paper production. The fibers suspended in water are pumped onto an oblique wire cloth. While the liquid flows off and/or is suctioned off using a vacuum, the fibers orient themselves on the surface of the wire cloth and are dried as fleece over a drying cylinder. Drying takes place at 125° C., until a final moisture of 0.5–1.5 weight-% is achieved. The suction and production speed are selected, at 2m per minute, such that a material is made that has a weight per surface area of 60 g/m$^2$.

The following are used as raw materials:

80 parts polyester fiber, 1.7/6 mm (DuPont company)

20 parts viscose fibers, 1.7/6 mm (Rohtex Textil company)

20 parts Kuralon® (polyvinylalcohol)(Rohtex Textil company)

Weight per surface area: 60 g/m$^2$
Thickness: 0.3 mm
Liquid absorption: 530 ml/m$^2$ Beside the sample collecting area (23), the sample collecting element (24) has two sample identification labels that contain data for sample identification in a bar code. At least one of the labels can be taken off. However, instead of two sample identification labels, it is also possible to use only one label with bar code. Preferably however, this one label is removable.

On the side of the closing flap (29) that is to be brought into contact with the back (30) of the envelope, there is an adhesive (27) that is used to close the envelope (21). Below the adhesive (27), there are two perforated lines (28) parallel to each other, which make it easier to open the closed envelope (21). On the inside of the closing flap (29), there is also information on the procedure for the person taking the sample. The envelope material consists of thin cardboard that is coated on both sides with a water-repellant material.

For the sake of completeness, FIG. 2B shows a view of the closed envelope.

When the article according to the invention is used as intended, the liquid sample to be tested, usually blood, but also other body fluids, e.g. urine, saliva or samples derived from the blood like plasma or serum are possible; is applied through the cut-out on the sample collecting element (24) onto the sample collecting area (23) of the absorbent matrix (22). If data are required for later identification of the sample, this data, e.g. patient address and name of the treating physician, can be noted on the sample collecting element (24) before or after the sample is applied.

The liquid sample penetrates quickly, i.e. within a few seconds, into the absorbent matrix and dries there. The envelope can then be closed. To do this the adhesive (27) is either moistened or revealed by pulling off a protective film. The inside of the closing flap (29) with the adhesive (27) is brought into contact with the back (30) of the envelope (21) so that the sample collecting element (24) is covered by the closing flap (29) in such a way that the sample collecting area (23) is no longer accessible from the outside and contamination can be prevented during transport. The envelope closed in this way is sent to a laboratory where the envelope can be opened by a strip that can be pulled out of the envelope along the perforated lines (28) and the closing flap (29) can thus be folded up again. The sample collecting element (24) that is made accessible again in this way with the sample collecting area (23) and the matrix (22) containing the sample is then separated along the perforated line (25) from the back (30) of the envelope in the laboratory. A part of the matrix (22) that is then freely accessible in the sample collecting area (23) is removed in order to elute the analyte to be determined. As a rule, a piece, usually a round piece of matrix (22) is removed in the area of the sample collecting area (23) using a hole punch. These punched samples are generally 3 to 8 mm, but they can be larger or smaller depending on the size of the sample collecting area (23) and the quantity of sample necessary to determine the analyte. At least one of the identification labels (26) is taken off the sample collecting element (24) and affixed to the vessel in which the part of the matrix (22) containing the sample is placed. Depending on the analyte to be determined, elution and analyte determining measures are initiated, which are known to the person skilled in the art.

The explanations above show that using the article according to the invention, a unit for collecting and transporting a sample to be analyzed is created that represents a simplification, compared to the state of the art, both for the patient as well as in the laboratory. The patient or physician need only apply the liquid sample on the sample collecting area of the article according to the invention, close the envelope and send it to the laboratory. It is no longer necessary to handle a collection card containing a sample when sliding it into an envelope. In the laboratory, it is also possible, without danger of contamination, to open the article according to the invention and take out the sample collecting element. Since the sample collecting element can not move in the envelope during transport, smearing of the sample on the inside of the envelope is prevented. In addition the patient and/or the physician who takes the sample has fewer parts to store and the danger of losing a part is prevented. Because of this, it is also no longer necessary to replace lost parts with others that are less suitable but happen to be on hand. So, for example, the invention insures that an envelope is used that is of a quality such that it does not have a deleterious effect on the analyte in the sample.

We claim:

1. An article of manufacture useful in collecting and transporting a liquid containing sample, comprising an envelope having a first area and a second area, said second area comprising a liquid absorbing matrix integral thereto and an area for receiving written information therein, said first and second areas joined by defined breaking or tearing lines along which the second area can be separated from said first area.

2. The article of manufacture of claim 1, wherein said second area is of a predetermined size.

3. The article of manufacture of claim 1, wherein said liquid absorbing matrix consists of material different from material of which the remainder of said second area is made.

4. The article of manufacture of claim 3 wherein the material of which said liquid adsorbing matrix consists is more absorbent than the remainder of said second area.

5. The article of manufacture of claim 1, wherein said breaking or tearing lines are perforated.

6. The article of manufacture of claim 1, wherein said first and second areas are joined along defined breaking or tearing lines comprising material having thinner cross section than material from said first and second areas which surround said breaking or tearing lines.

7. The article of manufacture of claim 1, wherein said written information is a series of written questions relating to patient information or sample data.

8. The article of manufacture of claim 1, wherein said second area further comprises at least one label containing further information.

9. The article of manufacture of claim 8, wherein said label is removable.

10. The article of manufacture of claim 8, wherein said label is in readable or coded form.

11. The article of manufacture of claim 1, further comprising raised, inert material positioned around said liquid absorbing matrix.

12. The article of manufacture of claim 1, further comprising a temperature sensor.

13. The article of manufacture of claim 1, further comprising a moisture sensor.

14. The article of manufacture of claim 1, wherein said liquid absorbing matrix comprises a synthetic fiber fleece.

15. The article of manufacture of claim 14, wherein said synthetic fiber fleece comprises a mixture of (i) cellulose based fibers, (ii) polymer fibers base in at least one of polyester and polyamide, and (iii) an organic binder which contains OH groups or ester groups.

16. The article of manufacture of claim 1, wherein said envelope further comprises an adhesive sealing means.

17. The article of manufacture of claim 1, further comprising a perforated flap for sealing said envelope.

18. The article of manufacture of claim 17, wherein said perforated flap comprises at least two lines of perforation positioned thereon.

* * * * *